United States Patent
Karp et al.

Patent Number: 5,576,286
Date of Patent: Nov. 19, 1996

[54] LIQUID POTPOURRI AND METHOD OF MANUFACTURE

[75] Inventors: Randy Y. Karp, Long Grove; Merle Tresser, Chicago, both of Ill.; John V. Pascale; Gregory S. Bennett, both of Granger, Ind.; Bruce Bennett, Barrington, Ill.

[73] Assignee: Scentex, Inc., Chicago, Ill.

[21] Appl. No.: 501,884

[22] Filed: Jul. 13, 1995

Related U.S. Application Data

[63] Continuation of Ser. No. 183,647, Jan. 18, 1994, abandoned.

[51] Int. Cl.$^6$ .................................................. A61K 7/46
[52] U.S. Cl. ............................................ 512/2; 512/3
[58] Field of Search ................................... 512/2, 3, 4

[56] References Cited

U.S. PATENT DOCUMENTS

| | | | |
|---|---|---|---|
| 2,927,055 | 3/1960 | Lanyest | 424/76.4 |
| 3,767,787 | 10/1973 | Segal | 512/4 |
| 4,067,824 | 1/1978 | Teng et al. | 424/76.4 |
| 4,071,616 | 1/1978 | Black | 424/76.4 |
| 4,128,507 | 12/1978 | Mitzner | 512/4 |
| 4,528,125 | 7/1985 | Alderman et al. | 512/4 |
| 4,719,040 | 1/1988 | Traas et al. | 512/4 |
| 5,051,305 | 9/1991 | Whitaker | 512/4 |
| 5,145,673 | 9/1992 | Roizumi | 424/76.4 |
| 5,238,915 | 8/1993 | Fuwa et al. | 512/4 |
| 5,246,919 | 9/1993 | King | 512/4 |

*Primary Examiner*—James H. Reamer
*Attorney, Agent, or Firm*—Welsh & Katz, Ltd.

[57] ABSTRACT

This invention relates to a novel formulation and its method of manufacture, for liquid potpourri utilizing a gelable acrylic acid copolymer, hydroxypropylcellulose, and a water or aqueous alcohol carrier, which form a polymer matrix when the pH raised to between 5 and 7. Encapsulated fragrance droplets are suspended in the matrix.

25 Claims, No Drawings

LIQUID POTPOURRI AND METHOD OF MANUFACTURE

This application is a FWC of 08/183,647, Jan. 18, 1994, now abandoned.

BACKGROUND OF THE INVENTION

Potpourri is a common and favored method for adding fragrance to the air. Potpourri comes in many forms and the fragrance is delivered to the air of a room via many different mechanisms.

One favored mechanism for delivering fragrance to the air is the use of liquid, or simmering, potpourri. Liquid potpourri is poured into a potpourri simmering pot and heated, generally by a small candle. The heat causes the fragrance to evaporate into the air. Although liquid potpourri has many advantages, there are also disadvantages to the known methods for producing and using liquid potpourri.

At the present time, most liquid potpourri is manufactured in a way that prohibits the use of many fragrance components and natural plant oils. The surfactants and emulsifiers necessary to keep the fragrance emulsified within the carrier also act to destroy many important fragrance components. Therefore, the perfumer is restricted to a limited odor/component pallet and cannot therefore produce many types of fragrances.

Additionally, traditional liquid potpourris often use chloride or ammonium compounds and surfactants that are hazardous to the environment, are extremely poisonous if swallowed, and cause damage to furniture if spilled. Many of the components in traditional liquid potpourri are also flammable and highly volatile. Traditional liquid potpourri also splashes quite easily, resulting in spills on furniture and on the users hands and clothing.

In addition, fragrances are often altered by exposure to light and heat and will also change over time. The current methods for producing liquid potpourri do not protect the fragrance from either light or heat, and while a container of liquid potpourri may begin as a nice fragrance, it will, over time, become rancid. The time period involved will vary depending upon how the fragrance is stored.

The nature of the type of fragrances used in present liquid potpourri results in the fragrance being introduced into the air unevenly since the fragrance evaporates or distills off unevenly. The top, most volatile, notes come off first, followed by the middle and then the low notes. Therefore, the fragrance in the air is distorted and differs from the scent developed by the perfumer. The scent must be carefully engineered to disguise this imperfect method of delivery.

The fragrance in existing systems is also delivered in an uncontrolled, uneven manner. As the liquid heats up, there is an initial burst of fragrance that raises the use's acuity level. Then, as the amount of fragrance in the air drops off, or remains constant the user is often unable to detect the scent at all. This is due to the fact that a person will become accustomed to a certain level of scent in the air and will, after a period of time, no longer be able to detect the same scent level.

The present invention eliminates each of these problems, resulting in a liquid potpourri that is able to utilize fragrances that include many more types of essential components and natural plant oils, is protected from conditions that may cause the fragrance to become rancid, and delivered in a way that does not distort the fragrance and results in an even, longer lasting, fragrance release.

In addition, the formula of the liquid potpourri of the present invention does not require surfactants or emulsifiers. There are no chloride or aluminum compounds present. The resulting product is safer for the user, is more environmentally safe and will cause much less damage to furniture if spilled. The potpourri of the present invention is thicker and therefore will not splash when poured reducing the possibility of furniture damage. The formula is also more economical to manufacture.

SUMMARY OF THE INVENTION

It is an object of the present invention to provide a liquid potpourri which includes fragrances manufactured from a wide variety of fragrance components which are difficult to emulsify and natural plant oils, thereby expanding the perfumer's odor/component pallet, and allowing the creation of more complex fragrances and a wider variety of fragrances. In addition, these fragrances do not need to be formulated to an exact distillation curve and are evaporated without distortion of the original intent.

It is a further object of this invention to create a liquid potpourri where the fragrance is protected from light, heat and water resulting in a liquid potpourri with a longer shelf life.

A further object of this invention is to provide a liquid potpourri with an improved delivery method resulting in the true fragrance being released without distortion, and resulting in a steady release of fragrance over an extended period of time.

A further object of the present invention is to create a liquid potpourri that does not require the use of surfactants or emulsifiers and is therefore safer for the user, more environmentally safe, less damaging to furniture and is not flammable or volatile.

The objects of this invention are met by the suspension of encapsulated fragrance droplets in a polymer solution which uses water, or an aqueous alcohol solution, as a carrier. The liquid potpourri of this invention is viscous and the fragrance capsules are suspended inside a polymer matrix in a uniform manner which protects the capsules from contacting each other and from contacting the packaging, thereby greatly reducing capsules breakage. In addition, the polymer matrix and the capsule protects the fragrance inside the capsule from exposure to damaging light and, to a certain extent, heat.

The viscous nature of the present liquid potpourri also acts to eliminate splashing when the product is poured. This feature further protects against damage to the user's hands and clothing, and protects against accidental ingestion of material spilled onto the users hands. Reduced splashing will also help reduce spillage on and damage to furniture.

The polymer matrix further acts to limit migration of water in the area immediately surrounding the capsules and therefore protects the capsules from contact with the water or aqueous alcohol carrier, thereby further macroencapsulating, with the polymer matrix, any fragrance that may migrate out of the capsule and into the carrier. The matrix also protects the capsules from dissolving in the water.

For these reasons, the liquid potpourri of the present invention is more stable and has a longer shelf life than traditional liquid potpourri.

The formula for the liquid potpourri of the present invention also provides greatly improved fragrance release. The potpourri of the present invention utilizes traditional potpourri simmering pots, heated with tea candles, or may be heated in a small pan on a stove. The container should be heated to between 60 and 70 degrees Celsius.

As the solution is heated, the viscosity of the potpourri lessens slightly and the capsules become more soluble in water. Due to the reduced viscosity the capsules come into contact with more water, or aqueous alcohol. This allows some fragrance molecules to migrate through the capsule wall. However, the majority of the fragrance is released when the capsule starts to dissolve and then breaks. The release of fragrance is controlled by the use of capsules with different wall thicknesses. The capsules will therefore break at different times, maintaining a constant fragrance release.

DETAILED DESCRIPTION OF THE PREFERRED EMBODIMENT

The liquid potpourri of the present invention consists of a solution comprised of the following compounds in the identified concentrations:

| COMPOUND | PERCENT BY VOLUME |
| --- | --- |
| Water (or Aqueous Alcohol) | 93.5–97.8% |
| Acrylic Acid Copolymer | 0.1–0.5% |
| Hydroxypropylcellulose | 1.0–3.0% |
| Encapsulated Fragrance | 1.0–2.0% |
| Triethanol Amine | 0.1–1.0% |
| Acid Dye | q.s. |

One specific example of liquid potpourri produced by the present invention would be as follows:

| COMPOUND | PERCENT BY VOLUME |
| --- | --- |
| Water (or Aqueous Alcohol) | 95.1% |
| Acrylic Acid Copolymer | 0.4% |
| Hydroxypropylcellulose | 2.0% |
| Encapsulated Fragrance | 2.0% |
| Triethanol Amine | 0.5% |
| Acid Dye | q.s. |

Both water and aqueous alcohol can be used with equal effectiveness. Product made with alcohol will have increased clarity. The concentration of the alcohol solution is not critical. Any concentration may be used.

The fragrance is encapsulated in a cross linked gelatin capsule. The capsule size ranges between 1500 and 3000 microns. Capsules of different sizes are present, preferably providing a range of capsule wall thicknesses. This range of wall thicknesses results in a steady release of fragrance due to the different time required for capsules with different wall thicknesses to dissolve.

The capsules are cross-linked gelatin manufactured using standard cross-linking gelatin technology. For example, the gelatin may be cross-linked with various dialdehydes, more specifically with glutaraldehyde. The preferred capsule is manufactured by a proprietary method performed by Arcade Encapsulated Products in Chattanooga, Tenn.

The fragrance contained within the capsule can be formulated with known techniques, but must be suitable for encapsulation into the cross-linked gelatin capsules. For example, the fragrance may be a mixture of odorous synthetic and natural oils soluble components which when combined have little or no water solubility and a specific gravity between 0.50 and 1.150. The preferred fragrance formulation is manufactured by LiBenn Aroma, Inc. in South Bend, Ind.

When mixed with water at a pH between 5 and 7 the hydroxypropylcellulose and the acrylic acid copolymer react to form a viscous polymer matrix. This matrix suspends the fragrance capsules protecting them as described above. The acrylic acid copolymer should be a gelable polymer of acrylic acid. The acrylic acid can be cross-linked using cross linking agents as are known in the art to produce a compound sufficiently water soluble to provide viscosity in gel form. The cross linking agent should contain at least 3 allyl groups per molecule.

Although it is anticipated that several polymers may provide similar results, the preferred polymer is produced by BF Goodrich under the trade name Carbopol 941 (CAS No. 9003-01-4). Other suggested polymers include BF Goodrich's Carbopol 940 and 934. Carpol 941 is a carbomer, i.e., a high molecular weight (1,250,000.) polymer of acrylic acid cross-linked with allyl ethers of pentaerythritol. Carpol 940 is also a carbomer, i.e., a high molecular weight (4,000,000) polymer of acrylic acid cross-linked with allyl ethers of pentaerythritol. Carpol 934 is a carbomer, i.e. a high molecular weight (3,000,000) polymer of acrylic acid cross-linked with allyl ethers of sucrose.

The use of hydroxypropylcellulose has been specifically disclosed, and is the preferred mechanism for thickening the acrylic acid copolymer. However it is anticipated that other hydroxyl donors will produce similar results. The preferred hydroxypropylcellulose is produced by Hercules, Inc. under the trade name Aqualon Klucel M.

To create the appropriate viscosity, the pH of the solution must be between 5 and 7. While there are many appropriate substances that may be used to increase the pH to the desired level, the preferred compound is triethanol amine.

The liquid potpourri of the present invention is produced by the following preferred method. Water, at room temperature, is placed into a container. Then Aqualon Klucel M, in an amount equal to between 1.0% to 3.0% of the total volume, is slowly added to the water, with stirring. The resulting mixture is stirred until the Klucel is evenly dispersed.

BF Goodrich's Carbopol 941 is added in an amount between 0.1% and 0.5% of the total volume and stirred until the Carbopol is evenly dispersed.

If it is desired that the potpourri have a color, an acid dye can be added at this time. The amount of the dye added will depend upon the depth of color desired.

After the dye is added, the fragrance, encapsulated within cross linked gelatin capsules, is added in an amount between 1% and 2% of the total volume. The fragrance capsules are stirred gently to disperse them throughout the solution, without breaking the capsule walls.

The pH of the solution is then adjusted to between 5 and 7 by the addition of triethanol amine in an amount between 0.1% and 1.0% of the total volume.

The resulting product is then packaged.

When the pH is properly adjusted, the Klucel and the Carbopol 941 form a latticework that surrounds each fragrance capsule. This latticework keeps the capsules from all sinking to the bottom of the package or later immediately to the bottom of the pot. It also keeps the capsules from contacting each other or the side of the packaging and breaking.

In addition, the matrix acts to limit the migration of water molecules. Although some water will be in contact with the capsules, the matrix limits the migration of water molecules from cell to cell. The same water will remain in the cell thereby acting to macroencapsulate any fragrance that has migrated out of the capsules. And, in time, the cell will stabilize and not allow any further migration of fragrance or degradation of the capsule.

The capsule surrounding the fragrance protects the fragrance from light and heat and also eliminates the need for surfactants and emulsifiers to keep free flowing fragrance emulsified in the liquid. The capsules preferably are present with a variety of wall thicknesses. There is preferably a controlled amount of each wall thickness which provides for a controlled, even release of fragrance.

In another preferred embodiment, the water carrier is replaced with an aqueous alcohol solution. The alcohol helps maintain the clarity of the solution and also aids in the release of the fragrance. The percent alcohol in the aqueous solution is not crucial. The method of manufacture is identical to the above described method, except that the starting material is an aqueous alcohol solution.

The fragrance contained in the cross linked gelatin capsules is released by heating the liquid potpourri to between 60 and 70 degrees Celsius. Heating will generally occur in a simmering potpourri pot with a small tea candle or possibly on a stove. As the solution heats up, it becomes less viscous and the capsules become more water soluble. Some additional fragrance molecules migrate through the capsule wall. However, the majority of the fragrance is not released until the capsules begin to dissolve and then break.

The fragrance is released into the solution at atmospheric pressure, and then into the air by a distillation process where the fragrance itself is vaporized. In addition, the fragrance molecules are carried into the air as the water and/or alcohol in the solution vaporizes. The fragrance release is time controlled due to the different wall thicknesses of the capsules. The thinner walled capsules will break first. The thicker walled capsules will then break in order of wall thickness. This results in a steady, controlled release of fragrance. The fragrance will be released in waves, as each group of capsules break. Preferably, the number of capsules with the same wall thickness will be balanced so that each wave of fragrance is of similar strength as the first. The size variations in the wall thickness should be such that the level of scent in the room declines before the next noticeable wave of scent is released.

The waves of fragrance released take the best advantage of the way a person perceives scent. If the level of a scent remains constant the user will become accustomed to it and no longer perceive the scent. However, if there is an increase in the scent level, or a slight decline followed by an increase in scent level, the user will continue to be able to detect the scent in the room. The formulation of the potpourri of the present invention releases the fragrance in waves so that the user is continually able to detect the scent.

The same effect would be achieved by continually increasing the fragrance level. However, this is not the most economical method for maintaining the user's ability to detect the scent.

The release of fragrance is also controlled by the temperature of the solution. As the temperature increases, the capsules will break sooner. In addition, the capsules closer to the bottom of the pot will break first, due to the higher temperature closer to the heat source. As the water evaporates, more capsules will be closer to the lower portion of the pot.

As each group of capsules break, a new wave of fragrance is emitted. Between each wave of fragrance are low points at which the user's acuity level is reset below that of the wave peaks. Therefore the user can notice the waves of fragrance and can continue to enjoy the fragrance for the entire time it is released.

Another advantage of the present invention is that since the fragrance is protected within capsules, more complex fragrances can be developed. The fragrance is not damaged during manufacture of the liquid potpourri and remains stable after packaging. Additionally, the fragrance can be developed so that the entire scent is released at one time, eliminating distortion of the scent by having the top notes of the scent distill off first, followed by the middle and then the low notes.

While preferred embodiments of the invention have been shown and described, it should be understood that there is no intent to limit the invention by such disclosure, but rather it is intended to cover all modifications and alternative constructions that fall within the spirit and scope of the invention as described in the following claims:

We claim:

1. A method for manufacturing a liquid potpourri having a long shelf-life comprising the steps of:
   a. adding water at room temperature to a container;
   b. adding slowly, while stirring, hydroxypropylcellulose in an amount equal to 1.0%–3.0% of the final volume;
   c. stirring until all of said hydroxypropylcellulose is evenly dispersed in said water;
   d. adding a polymer of acrylic acid cross-linked with allyl ethers of pentaerythritol or allyl ethers of sucrose in an amount between 0.1% and 0.5% of the total final volume and stirring until said copolymer is fully dispersed;
   e. adding water soluble polymer encapsulated fragrance droplets, in an amount equal to 1%–2% of the total volume and then stirring slowly and gently to disperse said capsules;
   f. adjusting the Ph of the liquid potpourri solution to between 5 and 7 to form a liquid potpourri which releases said fragrance only upon the application of heat between about 60° C. and about 70° C.

2. The method as described in claim 1 where the pH is adjusted by the addition of triethanol amine in an amount equal to between 0.1% and 1.0% of the total volume.

3. The method as described in claim 1 where an acid dye is added to the mixture to produce a desired color.

4. The method as claimed in claim 2 where said dye is added in the desired amount after addition of said acrylic acid copolymer but before addition of said encapsulated fragrance droplets.

5. The method as claimed in claim 1 where said encapsulated fragrance droplets are comprised of capsules with varying wall thicknesses.

6. The method as claimed in claim 1 where said hydroxypropylcellulose is added in an amount equal to 2.0% of the total volume of the solution.

7. The method as described in claim 1 where said gelable acrylic acid copolymer is added in an amount equal to 0.4% of the total volume of the solution.

8. The method as described in claim 2 where said triethanol amine is added in an amount equal to 0.5% of the total volume.

9. The method as described in claim 1 where said encapsulated fragrance is added in an amount equal to 2% of the total volume of the solution.

10. A method of manufacturing liquid potpourri having a long shelf-life comprising the steps of:
    a. adding an aqueous alcohol solution at room temperature to a container, said alcohol solution being any desired concentration;

b. adding slowly, while stirring, hydroxypropylcellulose in an amount equal to 1.0%–3.0% of the final volume;

c. stirring until all of said hydroxypropylcellulose is evenly dispersed in said aqueous alcohol solution;

d. adding a polymer of acrylic acid cross-linked with allyl ethers of pentaerythritol or allyl ethers of sucrose in an amount between 0.1% and 0.5% of the total final volume and stirring until said copolymer is fully dispersed;

e. adding water soluble polymer encapsulated fragrance droplets in an amount equal to 1%–2% of the total volume and then stirring slowly and gently to disperse said capsules;

f. adjusting the pH of the liquid potpourri solution to between 5 and 7 to form a liquid potpourri which releases said fragrance only upon the application of heat between about 60° .C and about 70° C.

11. The method as described in claim 10 where the pH is adjusted by the addition of triethanol amine in an amount equal to between 0.1% and 1.0% of the total volume of the solution.

12. The method as described in claim 10 where an acid dye is added to the mixture to produce a desired color.

13. The method as claimed in claim 12 where said dye is added in the desired amount after addition of said acrylic acid copolymer but before addition of said encapsulated fragrance droplets.

14. The method as described in claim 10 where said encapsulated fragrance droplets are comprised of capsules with varying wall thicknesses.

15. The method as claimed in claim 10 where said hydroxypropylcellulose is added in an amount equal to 2.0% of the total volume of the solution.

16. The method as described in claim 10 where said gelable acrylic acid copolymer is added in an amount equal to 0.4% of the total volume of the solution.

17. The method as described in claim 11 where said triethanol amine is added in an amount equal to 0.5% of the total volume.

18. The method as described in claim 10 where said encapsulated fragrance is added in an amount equal to 2% of the total volume of the solution.

19. A liquid potpourri solution having a long shelf-life and a pH between 5 and 7 comprising:

a. A polymer of acrylic acid cross-linked with allyl ethers of pentaerythritol or allyl ethers of sucrose in an amount between 0.1% and 0.5% of the total volume of said potpourri;

b. hydroxypropylcellulose in an amount between 1.0% and 3.0% of the total volume of said liquid potpourri solution;

c. water, in an amount between 94.0% and 97.8% of the total volume of said liquid potpourri solution;

d. water soluble polymer encapsulated fragrance droplets, in an amount between 1% and 2% of the total volume of said liquid potpourri solution, said fragrance being released on the application of heat between about 60° C. and about 70° C.

20. The liquid potpourri described in claim 19 where said pH is maintained between 5 and 7 by the addition of triethanol amine, in an amount between 0.1% and 1.0% of the total volume of said potpourri.

21. The liquid potpourri as described in claim 19 further comprising an acid dye in an amount necessary to produce a desired color.

22. The liquid potpourri as described in claim 19 wherein said water is replaced with an aqueous alcohol solution, said alcohol solution being any desired concentration.

23. The liquid potpourri described in claim 22 further comprising an acid dye in an amount necessary to produce a desired color.

24. The liquid potpourri described in claim 19 where said encapsulated fragrance droplets are comprised of capsules with different wall thicknesses.

25. The liquid potpourri described in claim 22 where said encapsulated fragrance droplets are comprised of capsules with different wall thicknesses.

* * * * *